United States Patent [19]

Kaiser et al.

[11] 4,073,912

[45] Feb. 14, 1978

[54] PIPERIDYLIDENE DERIVATIVES OF BENZO-FUSED XANTHENES, THIOXANTHENES AND DIBENZOXEPINS AND ANTIPSYCHOTIC USE THEREOF

[75] Inventors: Carl Kaiser, Haddon Heights, N.J.; John Joseph Lafferty, Levittown, Pa.

[73] Assignee: SmithKline Corporation, Philadelphia, Pa.

[21] Appl. No.: 731,254

[22] Filed: Oct. 12, 1976

[51] Int. Cl.$^2$ .................. C07D 405/04; C07D 409/04; A61K 31/445
[52] U.S. Cl. .............................. 424/267; 260/293.57; 260/293.58
[58] Field of Search ...................... 260/293.58, 293.57, 260/335, 328; 424/267

[56] References Cited

U.S. PATENT DOCUMENTS 3,275,640  9/1966  Engelhardt ...................... 260/293.4

OTHER PUBLICATIONS

Chemical Abstracts, vol. 64, Abstract No. 17548g and 17549g (1966).

*Primary Examiner*—Natalie Trousof
*Assistant Examiner*—Richard A. Schwartz
*Attorney, Agent, or Firm*—Joseph A. Marlino; Richard D. Foggio; William H. Edgerton

[57] ABSTRACT

Novel piperidylidene derivatives of benzo-fused xanthenes, thioxanthenes and dibenzoxepins administered internally to an animal host, in therapeutically effective amounts, produce antipsychotic activity essentially free of extrapyramidal symptoms.

12 Claims, No Drawings

PIPERIDYLIDENE DERIVATIVES OF BENZO-FUSED XANTHENES, THIOXANTHENES AND DIBENZOXEPINS AND ANTIPSYCHOTIC USE THEREOF

This invention relates to novel pharmaceutical compositions containing as an active ingredient compounds which produce antipsychotic activity essentially free of extrapyramidal symptoms and to a method of producing antipsychotic activity essentially free of extrapyramidal symptoms which comprises administering nontoxic effective quantities of said active ingredients to an animal. Extrapyramidal symptoms (EPS) are some of the most undesirable and common side effects produced by antipsychotic or neuroleptic drugs. The compounds which are the active ingredients used in the compositions and methods of this invention have a neuropharmacological profile indicative of potent antipsychotic activity but essentially no liability to produce EPS.

The active ingredients used in the compositions and methods of this invention are piperidylidene derivatives of benzo-fused xanthenes, thioxanthenes and dibenzoxepins of the following general formula:

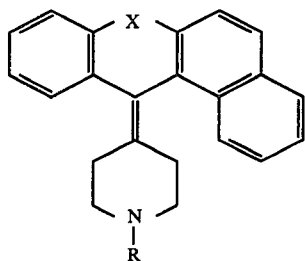

Formula 1 in which:

X represents oxygen, sulfur or methyleneoxy;

R represents hydrogen, lower alkyl or alkenyl of from 1 to 5 carbon atoms straight or branched chain, cycloalkylalkyl having from 4 to 8 carbon atoms, hydroxyalkyl of from 2 to 4 carbon atoms, acyloxyethyl of from 2 to 7 carbon atoms or

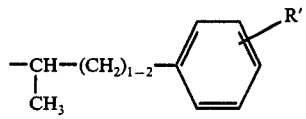

R' represents hydrogen, benzyloxy, hydroxy, methoxy or 3,4 methylenedioxy.

The nontoxic pharmaceutically acceptable acid addition salts of the compounds of formula 1 are similarly useful in the compositions and methods of this invention. Such salts are easily prepared by methods known to the art. The base is reacted with either the calculated amount of organic or inorganic acid in aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, pamoic, succinic, bismethylenesalicylic, acetylsalicylic, methanesulfonic, ethanedisulfonic, acetic, propionic, tartaric, salicylic, citric, gluconic, lactic, malic, mandelic, cinnamic, citraconic, cyclohexylsulfamic, aspartic, stearic, palmitic, itaconic, glycolic, p-aminobenzoic, glutamic, benzenesulfonic and theophyllineacetic acids as well as with 8-halotheophyllines, for example 8-bromotheophylline. Exemplary of such inorganic salts are those with hydrochloric, hydrobromic, sulfuric, phosphoric and nitric acids. Of course, these salts may also be prepared by the classical method of double decomposition of appropriate salts which is well known to the art.

The compounds of formula 1 where R is methyl are generally prepared from a benzo-fused derivative of xanthone, thioxanthone or dibenzoxepinone by reaction with an N-methylpiperidinyl magnesium halide in an inert organic solvent such as ether, for example ethyl ether, dioxane or tetrahydrofuran, at from room temperature to the reflux temperature of the solvent, for from 30 minutes to 4 hours. The carbinol intermediate is dehydrated to the olefin under acid or thermal conditions.

To prepare the compounds of formula 1 where R is other than methyl, the N-methylpiperidylidene derivative is treated with cyanogen bromide to give the N-cyanamide which is treated with acid to obtain the N-unsubstituted derivatives. The latter are N-alkylated by one of the following methods:

(a) direct alkylation with the appropriate alkyl, alkenyl, or aralkyl halide;

(b) acylation with the appropriate acyl chloride or anhydride to the corresponding amides followed by lithium aluminum hydride reduction; or (c) reaction with ethylene oxide.

There is evidence that antipsychotic drugs cause EPS by interfering with neurotransmission in a nigrostriatal dopaminergic pathway. It is thought that they block dopamine receptors in the neostriatum. Therefore, the ability of a drug to block striatal dopamine receptors is a measure of its EPS liability.

To assess the potency of drugs in blocking striatal dopamine receptors a procedure was used which was developed by Ungerstedt [Ungerstedt and Arbuthnott, Brain Res. 24 485 (1970); Ungerstedt, Acta physiol. scand., Suppl. 367, 49 (1971)] using rats with unilateral lesions of the substantia nigra induced by injection of 6-hydroxydopamine. This treatment causes degeneration of the nigrostriatal dopaminergic pathway accompanied by a marked decrease in the dopamine content of the neostriatum on the side of the lesion. Animals with this lesion develop postural and motor asymmetries which are altered by drugs which affect dopaminergic activity. Amphetamine, which releases dopamine and norepinephrine from catecholaminergic neurons, causes these rats to rotate unidirectionally toward the side of the lesion; i.e., ipsilaterally. Since there is a much larger amount of dopamine to be released by amphetamine from the intact nigrostriatal neurons on the non-lesioned side than from those remaining on the lesioned side, the rotational behavior is apparently due to a preponderance of activation of striatal dopamine receptors on the intact side. The ability of a drug to antagonize the rotational behavior is therefore a measure of its ability to block striatal dopamine receptors and is indicative of its potential to produce EPS.

To predict the potential ability of a drug to cause EPS, the ratio of its $ED_{50}$ (i.p.) for antagonism of amphetamine-induced rotation to its $ED_{50}$ (i.p.) for blockade of shock avoidance acquisition in the rat, a procedure for assessing antipsychotic activity, (R/A ratio) is calculated. The $ED_{50}$ values of some clinically established antipsychotics in the avoidance and rotational tests and the R/A ratios are presented in Table I.

Table I

| Drug | A<br>Antagonism of<br>Avoidance<br>Acquisition<br>Rats<br>$ED_{50}$ mg/kg (i.p.) | R<br>Antagonism of<br>Amphetamine-induced<br>Rotation<br>Rats<br>$ED_{50}$ mg/kg (i.p.) | R/A |
|---|---|---|---|
| Chlorpromazine | 1.5 | 2.0 | 1.3 |
| Trifluoperazine | 0.26 | 0.12 | 0.46 |
| Haloperidol | 0.16 | 0.05 | 0.31 |
| Pimozide | 0.24 | 0.08 | 0.30 |
| Thioridazine | 5.1 | 13.7 | 2.7 |
| Clozapine | 6.6 | 25.4 | 3.8 |

Chlorpromazine has a R/A ratio of 1.3. Antipsychotics that have a considerably greater propensity to cause EPS than chlorpromazine, e.g., trifluoperazine, haloperidol and pimozide, have ratios of 0.3 to 0.5. The two antipsychotics known to produce EPS to a lesser extent than chlorpromazine, i.e., thioridazine and clozapine, have ratios of 2.7 and 3.8, respectively. Therefore a high R/A ratio predicts that a drug will have a low potential to produce EPS.

A preferred compound of this invention is 12-(1-methyl-4-piperidylidene)-12H-benzo[a]xanthene hydrochloride which has an $ED_{50}$ of 0.64 mg./kg. (i.p.) for blockade of shock avoidance acquisition and an $ED_{50}$ of 6.4 mg./kg. (i.p.) for antagonism of amphetamine-induced rotation. The R/A ratio of 10 indicates that the above noted compound of this invention is essentially free of EPS liability.

The compositions of this invention are prepared in conventional dosage unit forms by incorporating a compound of formula 1 or a pharmaceutically acceptable salt thereof, in a nontoxic amount sufficient to produce antipsychotic activity without extrapyramidal symptoms in an animal, with a nontoxic pharmaceutical carrier according to accepted procedures. Preferably the compositions will contain the active ingredient in an active but nontoxic amount selected from about 1 mg. to about 300 mg., advantageously from about 5 mg. to about 200 mg., of active ingredient per dosage unit.

The pharmaceutical carrier employed may be, for example, either a solid or liquid, giving rise to a wide variety of pharmaceutical forms. If a solid pharmaceutical carrier is used, such as lactose, magnesium stearate, terra alba, sucrose, talc, stearic acid, gelatin, agar, pectin, acacia and the like, the composition can be tableted, used as a pharmaceutical powder, placed in a hard gelatin capsule or in the form of a troche or lozenge. The amount of solid carrier will vary widely but preferably will be from about 25 mg. to about 1 g. If a liquid pharmaceutical carrier is used, such as syrup, peanut oil, olive oil, sesame oil, water and the like, the composition will be in the form of a soft gelatin capsule, syrup, emulsion or a liquid suspension. Similarly the carrier or diluent may include a time delay material such as glyceryl monostearate or glyceryl distearate alone or with a wax.

Parenteral dosage forms such as for intramuscular administration are obtained by dissolving a water soluble salt of the active medicament in water or saline solution in a concentration such that 1 ml. of the solution contains from about 2 mg. to about 50 mg. of active ingredient. The solution can then be filled into single ampuls or multiple dose vials.

In accordance with the method of this invention a compound of formula 1 or a nontoxic acid addition salt thereof is administered internally to an animal in need of antipsychotic activity, preferably with a pharmaceutical carrier, in a nontoxic amount sufficient to produce antipsychotic activity essentially free of extrapyramidal symptoms. The active medicament, preferably in a dosage unit, is administered orally or intramuscularly in an active, nontoxic quantity selected from about 1 mg. to about 300 mg. of the parent chemical of formula 1. Advantageously, equal doses will be administered until a desired effect is obtained, such as two or three times a day. The daily dosage is selected from about 2 mg. to about 900 mg. of active medicament, advantageously from about 10 mg. to about 600 mg. When the method described above is carried out, antipsychotic activity is obtained with minimal EPS.

The following examples illustrate specific pharmaceutical compositions and their use in accordance with the method of this invention and as such are not to be considered as limitations thereof.

EXAMPLE 1

A well stirred mixture of 37.2 g. (0.15 mole) of o-iodobenzoic acid, 21.6 g. (0.15 mole) of β-naphthol and 20.6 g. (0.15 mole) of potassium carbonate in 300 ml. of pyridine is heated at 50° C. for 1 hour. Cuprous chloride (5 g.) is added and the mixture is refluxed for about 18 hours. The mixture is poured in 1200 ml. of water and filtered. The filtrate is acidified and extracted with methylene chloride. The extracts are dried, evaporated and the residue crystallized from carbon tetrachloride to yield 2-(2-naphthyloxy) benzoic acid.

A solution of 9.3 g. (0.035 mole) of 2-(2-naphthyloxy)benzoic acid in 30 ml. of polyphosphoric acid is heated to 135° C. with stirring for 3 hours. After cooling, water is added and the mixture is basified and extracted with a mixture of ethyl acetate and ether. The extracts are dried and the solvent evaporated. Recrystallization of the residue from ethanol yields 12-benzo[a]xanthone having a melting point of 139°–142° C.

Several drops of ethyl bromide are added to a stirred suspension of 4.3 g. (0.175 g.-atom) of magnesium turnings in 5 ml. of tetrahydrofuran under a nitrogen atmosphere. After the reaction begins, 29.8 g. (0.175 mole) of 4-chloro-1-methylpiperidine in 50 ml. of tetrahydrofuran is added. After the addition is complete the mixture is stirred, refluxed for 1 hour and cooled to 0° C.

To the chilled suspension of the Grignard reagent is added a slurry of 7.0 g. (0.028 mole) of 12-benzo[a]xanthone in 200 ml. of tetrahydrofuran. The solution is stirred for 1 hour at 0° C. and then poured into aqueous ammonium chloride and extracted with ether. The extracts are washed with water, dried and the solvent evaporated. The residue is crystallized from acetonitrile to give 12-hydroxy-12-(1-methyl-4-piperidinyl)benzo[a]xanthone having a melting point of 206°–208° C.

A solution of 12.5 g. (0.036 mole) of 12-hydroxy-12-(1-methyl-4-piperidinyl)benzo[a]xanthone and 12.5 g. of o-sulfobenzoic anhydride in 100 ml. of propionic acid is refluxed for 2 hours. The solvent is evaporated and the residue treated with 2.5 N sodium hydroxide and extracted with ether. The extracts are dried and the solvent evaporated. The residue is chromatographed over an alumina column using ether as the eluant. The product is collected in the first fraction, converted to the hydrochloride salt with ethereal hydrogen chloride, and recrystallized from ethanol to yield 12-(1-methyl-4-piperidylidene)-12H-benzo[a]xanthene hydrochloride hydrate having a melting point of 196°–200° C.

EXAMPLE 2

To a stirred solution of 10.6 g. (0.1 mole) of cyanogen bromide in 200 ml. of benzene is added dropwise 26.2 g. (0.08 mole) of 12-(1-methyl-4-piperidylidene)-12H-benzo[a]xanthene in 150 ml. of benzene. The mixture is heated at 50°-55° C. for 5 hours, filtered, and the filtrate extracted with 1 N phosphoric acid. The benzene solution is dried and concentrated to give a solid residue. Recrystallization from acetonitrile yields 12-(1-cyano-4-piperidylidene)-12H-benzo[a]xanthene.

A mixture of 16.9 g. (0.05 mole) of 12-(1-cyano-4-piperidylidene)-12H-benzo[a]xanthene, 400 ml. of acetic acid and 40 ml. of 12 N hydrochloric acid is stirred and refluxed for 20 hours. The resulting solution is evaporated in vacuo leaving a solid residue of 12-(4-piperidylidene)-12H-benzo[a]xanthene hydrochloride. A suspension of the hydrochloride in water is made alkaline with aqueous ammonia and the resultant base is extracted into ether. The ether solution is concentrated to give crystalline 12-(4-piperidylidene)-12H-benzo[a]xanthene.

EXAMPLE 3

A mixture of 15.7 g. (0.05 mole) of 12-(4-piperidylidene)-12H-benzo[a]xanthene, 3.1 g. (0.025 mole) of allyl bromide and 50 ml. of benzene is stirred at 25° C. for 2 hours. The mixture is diluted with ether and filtered to remove 12-(4-piperidylidene)-12H-benzo[a]xanthene hydrobromide. The filtrate is concentrated and the residue in ethanol is treated with ether and hydrogen chloride to give a solid which is recrystallized from methanol-ether to give colorless crystals of 12-(1-allyl-4-piperidylidene)-12H-benzo[a]xanthene hydrochloride.

EXAMPLE 4

A mixture of 15.7 g. (0.05 mole) of 12-(4-piperidylidene)-12H-benzo[a]xanthene, 11.0 g. (0.25 mole) of ethylene oxide and 300 ml. of methanol is stirred at 25° C. for 16 hours. Concentration of the resulting solution affords 12-[1-(2-hydroxyethyl)-4-piperidylidene]-12H-benzo[a]xanthene.

EXAMPLE 5

A mixture of 3.13 g. (0.01 mole) of 12-(4-piperidylidene)-12H-benzo[a]xanthene, 0.7 (0.005 mole) of 3-bromopropanol and 50 ml. of benzene is stirred and refluxed for 24 hours. The mixture is cooled, diluted with ether and the precipitated 12-(4-piperidylidene)-12H-benzo[a]xanthene hydrobromide is filtered. Concentration of the filtrate affords 12-[1-(3-hydroxypropyl)-4-piperidylidene]-12H-benzo[a]xanthene which is purified by fractional crystallization.

EXAMPLE 6

A solution of 15.7 g. (0.05 mole) of 12-(4-piperidylidene)-12H-benzo[a]xanthene and 2.61 g. (0.025 mole) of cyclopropanecarbonyl chloride in 50 ml. of benzene is stirred at ambient temperature for 2 hours. Ether is added to the mixture and the precipitated 12-(4-piperidylidene)-12H-benzo[a]xanthene hydrochloride is filtered. The filtrate is washed with 1 N phosphoric acid, then the organic layer is dried over magnesium sulfate and concentrated to give 12-(1-cyclopropylcarbonyl-4-piperidylidene)-12H-benzo[a]xanthene.

To a stirred suspension of 3.8 g. (0.1 mole) of lithium aluminum hydride in 250 ml. of ether is added dropwise a solution of 7.6 g. (0.002 mole) of 12-(1-cyclopropylcarbonyl-4-piperidylidene)-12H-benzo[a]xanthene in 50 ml. of tetrahydrofuran. The mixture is stirred and refluxed for 4 hours, then 3.8 ml. of water, 3.8 ml. of 2.5 N sodium hydroxide and 12 ml. of water are cautiously added dropwise in sequence. The mixture is filtered and the filtrate is concentrated. The residue is dissolved in ethanol and ethereal hydrogen chloride is added to give pH 3-4. Addition of ether precipitates a solid which is filtered and recrystallized from methanol-ether to give 12-(1-cyclopropylmethyl-4-piperidylidene)-12H-benzo[a]xanthene hydrochloride as colorless crystals.

EXAMPLE 7

A stirred solution of 16.9 g. of 12-(4-piperidylidene)-12H-benzo[a]xanthene (0.05 mole) in 100 ml. of acetic anhydride is heated at 100° C. for 3 hours, then it is concentrated under reduced pressure to remove excess acetic anhydride and acetic acid. The residue is taken into methylene chloride and the solution is washed several times with 1 N hydrochloric acid. After the methylene chloride solution is dried over magnesium sulfate, it is concentrated to leave a solid residue which is recrystallized from ethyl acetate-hexane to give 12-(1-acetyl-4-piperidylidene)-12H-benzo[a]xanthene, which is reduced with lithium aluminum hydride as described in Example 6 to give 12-(1-ethyl-4-piperidylidene)-12H-benzo[a]xanthene.

EXAMPLE 8

A mixture of 3.13 g. (0.01 mole) of 12-(4-piperidylidene)-12H-benzo[a]xanthene, 2.61 g. (0.01 mole) of 4-benzyloxyphenyl-2-chloropropane and 50 ml. of benzene is stirred and refluxed for twenty-four hours. After the mixture is cooled, it is diluted with ether and filtered to give 12-[4-[(4-benzyloxyphenyl-2-propyl)-4-piperidylidene]]-12H-benzo[a]xanthene hydrochloride. A suspension of this salt in water is made alkaline with aqueous ammonia and the mixture is extracted with ether. The ethereal solution is dried and concentrated to leave the base.

Similar alkylation of 12-(4-piperidylidene)-12H-benzo[a]xanthene with 4-methoxyphenyl-2-chloropropane or 3,4-methylenedioxyphenyl-2-chloropropane gives 12-[4-[(4-methoxyphenyl-2-propyl)-4-piperidylidene]]-12H-benzo[a]xanthene and 12-[4-[(3,4-methylenedioxyphenyl-2-propyl)-4-piperidylidene]]-12H-benzo[a]xanthene, respectively.

EXAMPLE 9

A mixture of 5.4 (0.01 mole) of 12-[4-[(4-benzyloxyphenyl-2-propyl)-4-piperidylidene]]-12H-benzo[a]xanthene, 1.0 g. of 10% palladium-on-carbon catalyst and 100 ml. of ethanol is hydrogenated on a Parr apparatus at ambient temperature and an initial hydrogen pressure of 60 p.s.i. After hydrogen uptake is complete, the mixture is filtered and the filtrate is concentrated in vacuo. A solution of the residue in methanol is adjusted to pH 3-4 with hydrogen chloride and ether is added to precipitate the product. Recrystallization from methanol-ether affords colorless crystals of 12-[4-[(4-hydroxyphenyl-2-propyl)-4-piperidylidene]]-12H-benzo[a]xanthene hydrochloride.

EXAMPLE 10

A solution of 12-[1-(2-hydroxyethyl-4-piperidylidene)]-12H-benzo[a]xanthene (7.15 g., 0.002 mole) in 100 ml. of acetic anhydride is heated at 100° C. for 2 hours. Excess acetic anhydride and acetic acid are removed by concentration in vacuo. The residue is taken into a mixture of ether and dilute aqueous ammonia. Concentration of the magnesium sulfate dried ether solution affords 12-[1-(2-acetoxyethyl-4-piperidylidene)]-12H-benzo[a]xanthene.

EXAMPLE 11

A solution of 7.15 g. (0.002 mole) of 12-[1-(2-hydroxyethyl)-4-piperidylidene]-12H-benzo[a]xanthene and 3.0 g. (0.002 mole) of heptanoyl chloride in 100 ml. of methylene chloride is stirred at 25° C. for 6 hours. The solution is concentrated in vacuo and the residual solid is recrystallized to give 12-(1-heptanoyloxyethyl-4-piperidylidene)-12H-benzo[a]xanthene hydrochloride.

EXAMPLE 12

A well stirred mixture of 37.2 g. (0.15 mole) of o-iodobenzoic acid, 34.0 g. (0.15 mole) of 2-mercaptonaphthalene, 20.6 g. (0.15 mole) of potassium carbonate and 300 ml. of pyridine is heated at 50° C. for 1 hour, then 5 g. of cuprous chloride is added and the stirred mixture is heated at reflux for 18 hours. The mixture is poured into 1.2 liters of water and filtered. The filtrate is acidified and the resulting mixture is extracted into methylene chloride. The extracts are dried, concentrated, and the solid residue is recrystallized to give 2-(2-naphthylthio)benzoic acid.

A stirred solution of 28.0 g. (0.1 mole) of 2-(2-naphthylthio)benzoic acid in 100 ml. of polyphosphoric acid is heated at 135° C. for 3 hours. After being cooled, water is added to the reaction product, the mixture is made alkaline with 10 N sodium hydroxide (with cooling) and the product is extracted into ethyl acetate. The extracts are dried over magnesium sulfate and then the solvent is evaporated. Recrystallization of the residue affords 12-benzo[a]thioxanthone.

Several drops of ethyl bromide are added to a stirred suspension of 2.43 g. (0.1 g.-atom) of magnesium turnings in 5 ml. of tetrahydrofuran under a nitrogen atmosphere. After the reaction begins, 13.4 g. (0.1 mole) of 4-chloro-1-methylpiperidine in 50 ml. of tetrahydrofuran is added at a rate which maintains reflux. After the addition is complete the mixture is stirred and refluxed for 1 hour and cooled to 0° C. To the chilled suspension is added 26.2 g. (0.1 mole) of 12-benzo[a]thioxanthone and the mixture is stirred and refluxed for 2 hours and then poured into a solution of 26.5 g. (0.5 mole) of ammonium chloride in 500 ml. of ice water. The mixture is extracted with methylene chloride; the extracts are dried and concentrated to yield 12-hydroxy-12-(1-methyl-4-piperidinyl)benzo[a]thioxanthene.

A solution of 12.9 g. (.036 mole) of 12-hydroxy-12-(1-methyl-4-piperidinyl)benzo[a]thioxanthene and 12.5 g. of o-sulfobenzoic anhydride in 100 ml. of propionic acid is refluxed for 2 hours. The solvent is evaporated and the residue treated with 2.5 N sodium hydroxide and extracted with ether. The extracts are dried and the solvent evaporated. The residue is chromatographed over an alumina column using ether as the eluant. The product is collected in the first fraction and recrystallized from ethanol to yield 12-(1-methyl-4-piperidylidene)-12H-benzo[a]thioxanthene.

EXAMPLE 13

To a stirred suspension of 9.6 g. (0.2 mole) of a 50% dispersion of sodium hydride in mineral oil in 60 ml. of dimethylformamide is added dropwise a solution of 28.8 g. (0.2 mole) of 2-naphthol in 100 ml. of dimethylformamide at such a rate that the temperature does not exceed 25° C. After hydrogen evolution is complete, 26.8 g. (0.2 mole) of phthalide in 100 ml. of dimethylformamide is added dropwise and the stirred mixture is heated under reflux for 2 hours. The solvent is distilled off and the residue is diluted with ice-water. The mixture is extracted with ether and then the aqueous portion is made acidic with 12 N hydrochloric acid. The crystalline precipitate is filtered and recrystallized from aqueous ethanol, using decolorizing carbon to give 2-(2-carboxybenzyloxy)naphthalene.

A mixture of 27.8 g. (0.1 mole) of 2-(2-carboxybenzyloxy)naphthalene, 50 g. of Super-cel and 200 mg. of xylene is stirred while being refluxed azeotropically. After all the water is removed, 50 g. of phosphorus pentoxide, along with sufficient xylene to facilitate stirring, is added. The mixture is stirred and refluxed for 24 hours, then it is cooled and filtered. The filtrate is concentrated in vacuo and the solid residue is recrystallized from 2-propanol to give crystalline 13-oxo-8,13-dihydrobenzo[e]naphth[2,1-b]oxepin.

Several drops of ethyl bromide are added to a stirred suspension of 2.43 g. (0.1 g.-atom) of magnesium turnings in 5 ml. of tetrahydrofuran under a nitrogen atmosphere. After the reaction begins, 13.4 g. (0.1 mole) of 4-chloro-1-methylpiperidine in 50 ml. of tetrahydrofuran is added at a rate which maintains reflux. After the addition is complete, the mixture is stirred and refluxed for 1 hour, then it is cooled to 0° C. and 26.0 g. (0.1 mole) of 13-oxo-8,13-dihydrobenzo[e]naph[2,1-b]oxepin is added in portions. The mixture is stirred and refluxed for 2 hours and then it is poured into a solution of 26.5 g. (0.5 mole) of ammonium chloride in 500 ml. of ice-water. The mixture is extracted with methylene chloride. The extracts are dried and concentrated to leave 13-hydroxy-13-(1-methyl-4-piperidinyl)-8,13-dihydrobenzo[e]naphth[2,1-b]oxepin as a solid residue which is purified by recrystallization from ethyl acetate-hexane.

13-Hydroxy-13-(1-methyl-4-piperidinyl)-8,13-dihydrobenzo[e]naphth[2,1-b]oxepin (18.0 g., 0.05 mole) is dissolved in 250 ml. of propionic acid and 27.6 g. (0.15 mole) of o-sulfobenzoic anhydride is added. After being refluxed for 30 minutes, the mixture is poured into an excess of ice-10 N sodium hydroxide. The mixture is extracted with ether. After being dried over magnesium sulfate, the ether extracts are concentrated. The residue is taken into ether and ethereal hydrogen chloride is added to give pH 3–4. Addition of ether produces a precipitate which is filtered and recrystallized from methanol-ether to give colorless crystals of 13-(1-methyl-4-piperidylidene)-8,13-dihydrobenz[e]naphth[2,1-b]oxepin hydrochloride.

EXAMPLE 14

| Ingredients | Mg. per capsule |
| --- | --- |
| 12-(1-Methyl-4-piperidylidene)-12H-benzo[a]xanthene Hydrochloride | 50 |
| Magnesium stearate | 2 |
| Lactose | 200 |

The above ingredients are mixed, passed through a #40 mesh screen, remixed and filled into #2 capsules.

EXAMPLE 15

| Ingredients | W/V percentages |
|---|---|
| 12-(1-Methyl-4-piperidylidene)-12H-benzo[a]xantheen | Equivalent to 20 mg of free base per ml. |
| Sodium tartrate | 1 |
| Tartaric acid | 0.7 |
| Water for parenterals, q.s. | 100 |

The above ingredients are dissolved in an amount of the water equal to approximately 95% of the final volume, mixed, heated as required, cooled to room temperature and the remainder of water is added. The solution is filtered and filled in ampuls.

The capsules or solution prepared as in Examples 14 or 15 are administered internally to an animal requiring antipsychotic activity within the dose ranges set forth hereinabove. Similarly other compounds of Formula 1 can be formulated in the same manner to give pharmaceutical compositions useful in the methods of this invention.

What is claimed is:

1. A chemical compound of the formula:

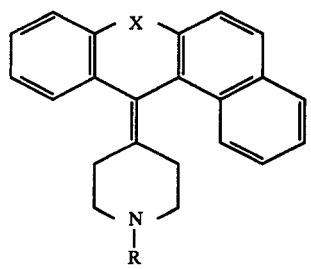

or a pharmaceutically acceptable acid addition salt thereof in which:

X is oxygen, sulfur or methyleneoxy; and

R is hydrogen, lower alkyl or alkenyl of from 1 to 5 carbon atoms, straight or branched chain, cycloalkylalkyl having 4 to 8 carbon atoms, hydroxyalkyl having from 2 to 4 carbon atoms, acyloxyethyl of from 2 to 7 carbon atoms or

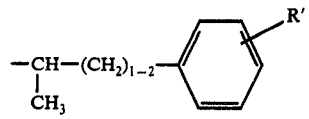

R' is hydrogen, benzyloxy, hydroxy, methoxy or 3,4-methylenedioxy.

2. A chemical compound in accordance with claim 1 in which X is oxygen.

3. A chemical compound in accordance with claim 2 in which R is lower alkyl.

4. A chemical compound in accordance with claim 3 in which R is methyl.

5. A pharmaceutical composition having antipsychotic activity essentially free of extrapyramidal symptoms in dosage unit form which comprises a pharmaceutical carrier and an antipsychotically effective amount of a compound according to claim 1 or a nontoxic pharmaceutically acceptable acid addition salt of said compound.

6. A pharmaceutical composition according to claim 5 in which the compound is 12-(1-methyl-4-piperidylidene)-12H-benzo[a]xanthene.

7. A pharmaceutical composition according to claim 6 in which the compound is in the form of the hydrochloride salt.

8. A pharmaceutical composition according to claim 5 in which the active ingredient is in an amount of from about 1 mg. to about 300 mg. per dosage unit.

9. A method of producing antipsychotic activity essentially free of extrapyramidal symptoms which comprises administering internally to an animal host in need of such activity a therapeutically effective amount of the compound of claim 1 or a nontoxic pharmaceutically acceptable acid addition salt thereof.

10. A method according to claim 9 in which the compound is 12-(1-methyl-4-piperidylidene)12H-benzo[a]xanthene.

11. A method according to claim 10 in which said compound is in the form of a hydrochloride salt.

12. A method according to claim 9 in which said compound is administered in a daily dose of from about 2 mg. to about 900 mg.

* * * * *